United States Patent
Xu

(10) Patent No.: US 10,221,155 B2
(45) Date of Patent: Mar. 5, 2019

(54) METHOD FOR PREPARING ALECTINIB

(71) Applicant: SUZHOU MIRACPHARMA TECHNOLOGY CO., LTD., Suzhou, Jiangsu Province (CN)

(72) Inventor: Xuenong Xu, Jiangsu (CN)

(73) Assignee: SUZHOU MIRACPHARMA TECHNOLOGY, CO., LTD., Suzhou, Jiangsu Province (CN)

( * ) Notice: Subject to any disclaimer, the term of this patent is extended or adjusted under 35 U.S.C. 154(b) by 0 days.

(21) Appl. No.: 15/524,749

(22) PCT Filed: Sep. 16, 2015

(86) PCT No.: PCT/CN2015/089736
§ 371 (c)(1),
(2) Date: May 5, 2017

(87) PCT Pub. No.: WO2016/074532
PCT Pub. Date: May 19, 2016

(65) Prior Publication Data
US 2017/0247352 A1    Aug. 31, 2017

(30) Foreign Application Priority Data
Nov. 12, 2014  (CN) .......................... 2014 1 0635005

(51) Int. Cl.
*C07D 413/14*  (2006.01)
*C07D 401/04*  (2006.01)

(52) U.S. Cl.
CPC .................................. *C07D 401/04* (2013.01)

(58) Field of Classification Search
CPC ...................................................... C07D 413/14
See application file for complete search history.

(56) References Cited

U.S. PATENT DOCUMENTS

2012/0083488 A1   4/2012  Chugai et al.
2013/0143877 A1   6/2013  Furumoto et al.

FOREIGN PATENT DOCUMENTS

CN      104402862      3/2015
JP      2012126711 A   7/2012

OTHER PUBLICATIONS

English Translation of International Search Report dated Dec. 15, 2015.

*Primary Examiner* — Bruck Kifle
(74) *Attorney, Agent, or Firm* — JK Intellectual Property Law, PA

(57) ABSTRACT

A method for preparing Alectinib (Alectinib, I), comprising the preparation steps: subjecting 6-cyano-1H-indole-3-carboxylate and 4-ethyl-3-(4-morpholine-4-yl-piperidine-1-yl)-α,α-dimethylbenzyl alcohol to condensation, hydrolyzing and cyclization reaction so as to prepare Alectinib (I). The preparation method has easily available raw materials and a simple process, and is economical and environmentally friendly and suitable for industrial production.

10 Claims, No Drawings

METHOD FOR PREPARING ALECTINIB

CROSS-REFERENCE TO RELATED APPLICATIONS

This application is a national stage of International Application No. PCT/CN2015/089736, filed Sep. 16, 2015 and claims benefit to Chinese Patent Application No. 201410635005.1 filed Nov. 12, 2014, both of which are incorporated by reference herein.

TECHNOLOGY FIELD

This invention belongs to the technology field of organic synthetic route design and preparation of its active pharmaceutical ingredients and intermediates, which particularly relates to the preparation method of a drug used for treatment of non-small cell lung cancer, Alectinib.

BACKGROUND

Alectinib, which is developed by the branch company of Roche in Japan, Chugai Pharmaceutical, is a new anaplastic lymphoma kinase (ALK) inhibitor, and is used for the treatment of ALK gene rearrangement non-small cell lung cancer patients. As it acts on the Crizotinib-resistant patients as well, and can reduce the brain metastases significantly, this drug was granted the status of "breakthrough therapeutic drug" by FDA of America in September 2013, and permitted to come to the market in July 2014 in Japan.

The chemical name of Alectinib is: 9-ethyl-6,6-dimethyl-8-(4-morpholin-4-o-piperidin-1-yl)-11-oxo-6,11-dihydro-5H-benzo[b]carbazole-3-carbonitrile (I), and its structural formula is:

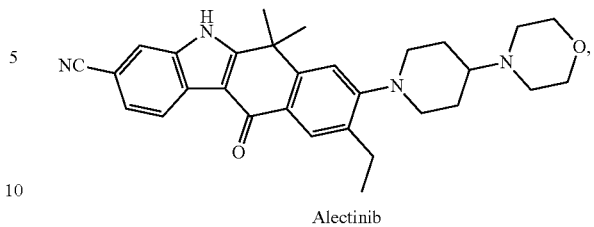

Alectinib

The PCT patents WO2010143664 and WO2012023597 of the original research & development Company and such documents as Page 1271-1280, Volume 20, Bioorganic & Medicinal Chemistry, 2012 and Page 6286-6294, Volume 54, J. Med. Chem., 2011 all have reported the synthetic methods of Alectinib. Its preparation mainly has two synthetic routes.

The first route takes 7-methoxyl-3,4-dihydronaphthalene-2(1H)-ketone (1) as the starting materials, and goes through the bis-methylation reaction (step 1), the 6-bromo reaction (step 2) and the cyclization reaction of hydrazine (step 3) to obtain the intermediate, 6,6-dimethyl-8-methoxyl-9-bromo-11-oxo-6,11-dihydro-5H-benzo[b]carbazole-3-carbonitrile (4) (step 4). Then, the intermediate 4 goes through methoxylhy drolysis (step 5), trifluoromethanesulfonic acid esterification (step 6) and condensation with the piperidin ring to obtain the intermediate, 6,6-dimethyl-8-(4-morpholinopiperidin-1-yl)-9-bromo-11-oxo-6,11-dihydro-5H-benzo[b]carbazole-3-carbonitrile (7) (step 7); the intermediate 7 goes through coupling reaction with (triisopropylsilicyl) acetylene under the actions of palladium catalyst, 2-dicyclohexylphosphin-2,4,6-triisopropylbiphenyl ligands and cesium carbonate etc. to generate the alkyne derivative (8); then the compound 8 will be reduced to ethyl by the alkynyl to obtain the target compound, Alectinib (I).

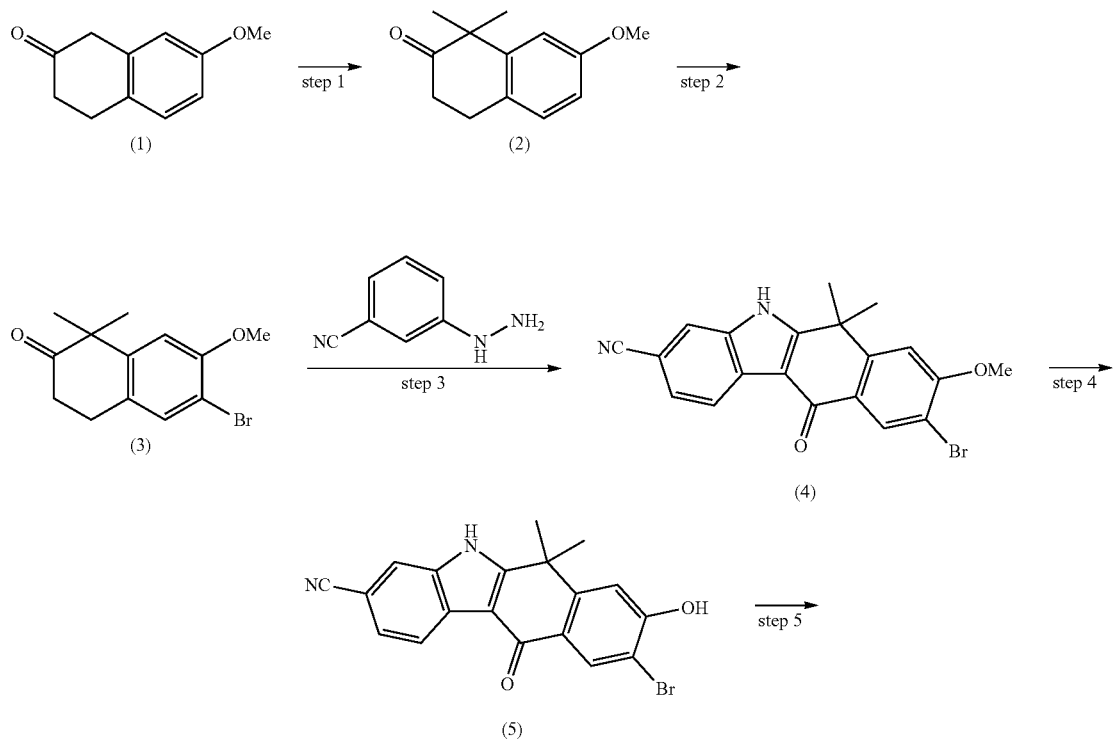

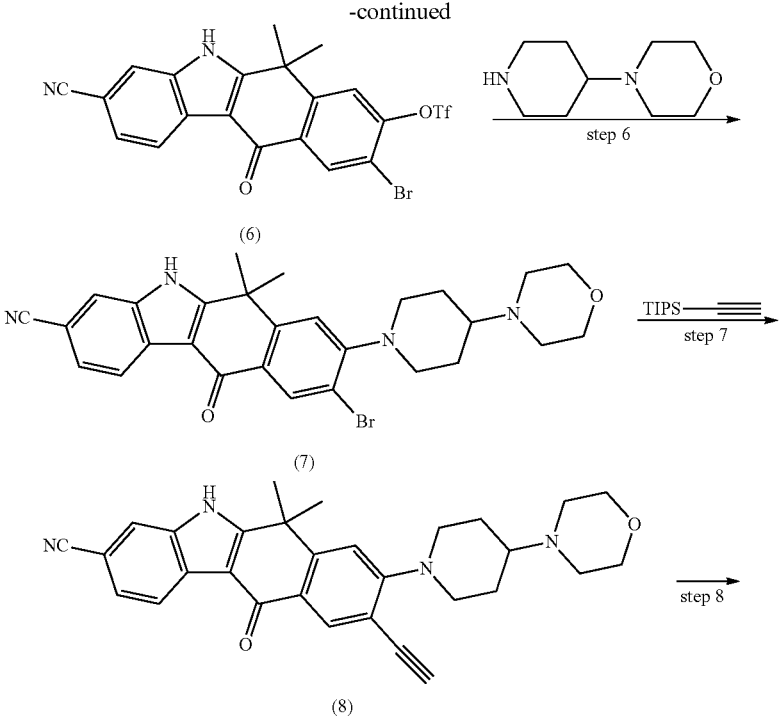

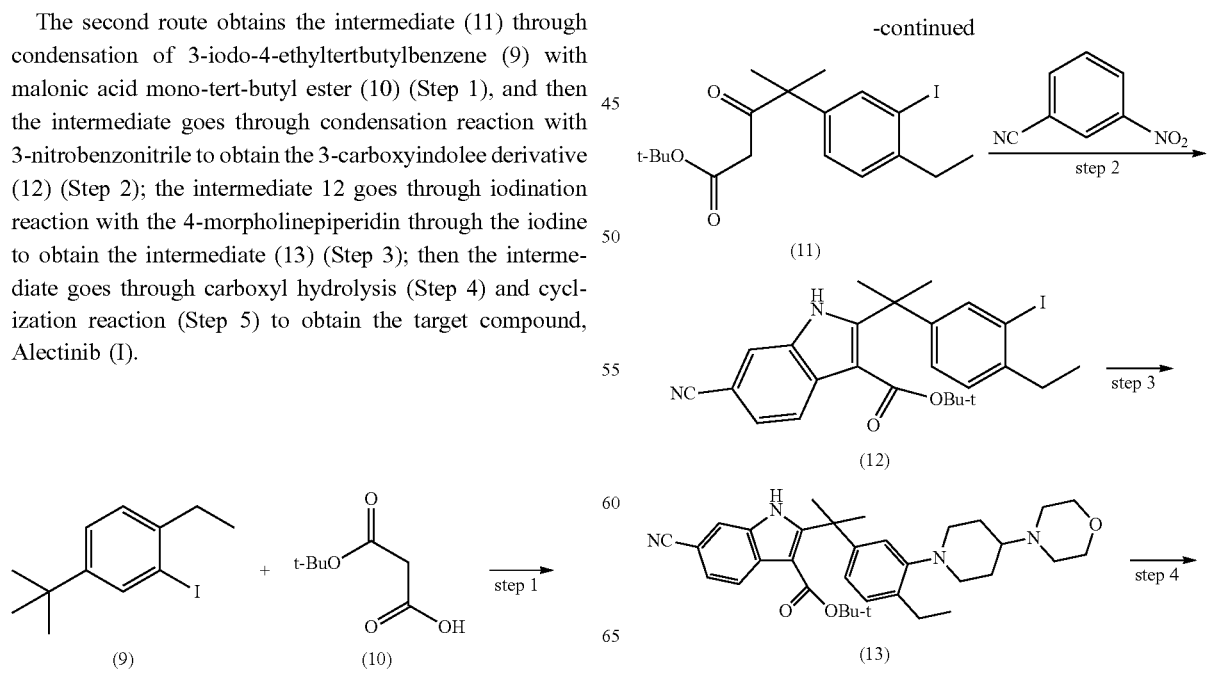

The second route obtains the intermediate (11) through condensation of 3-iodo-4-ethyltertbutylbenzene (9) with malonic acid mono-tert-butyl ester (10) (Step 1), and then the intermediate goes through condensation reaction with 3-nitrobenzonitrile to obtain the 3-carboxyindolee derivative (12) (Step 2); the intermediate 12 goes through iodination reaction with the 4-morpholinepiperidin through the iodine to obtain the intermediate (13) (Step 3); then the intermediate goes through carboxyl hydrolysis (Step 4) and cyclization reaction (Step 5) to obtain the target compound, Alectinib (I).

-continued

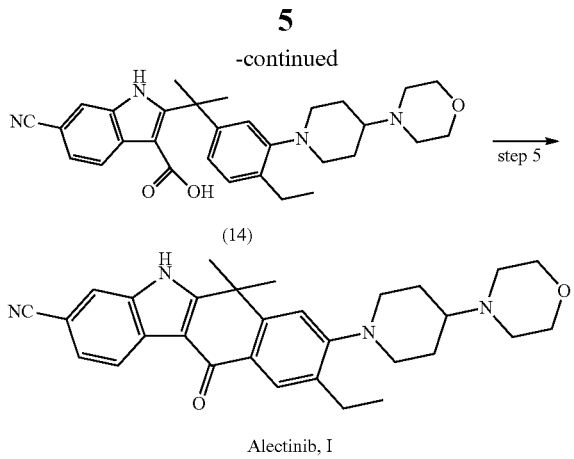

Alectinib, I

Through analysis of the above two synthetic routes, formation step of the core indolee ring adopts condensation of hydrazine and carbonyl (Step 3 in route I) or condensation of nitro (amino after reduction) and carbonyl (Step 2 in route II) respectively. As the two substrates contain multiple functional groups such as halogen, carbonyl, carboxyl, amino and cyano, the reaction process is fairly complicated with increased side reactions and purification difficulty; besides, most of the reaction materials and intermediates are difficult to get. Therefore, with respect to the defects of the current processes, developing a simple and direct, economic and environment-friendly preparation technology with high quality, particularly seeking a process technology that is adaptable to the industrialized production, is of great realistic significance to the improvement of the drug's economic and social benefits.

SUMMARY

This invention aims to provide an economic and environment-friendly preparation method for Alectinib, which is suitable for industrialized production and has good availability of raw materials and simple and direct processes.

To achieve the above-mentioned purposes, the invention adopts the following main technical scheme: a preparation method for Alectinib (Alectinib, I)

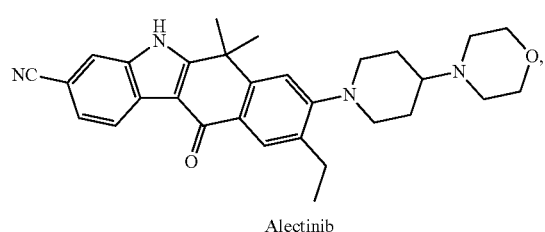

Alectinib

The preparation steps comprise: Use 6-cyano-1H-indole-3-carboxylic acid methyl ester or 6-cyano-1H-indole-3-carboxylic acid ethyl ester (II) to go through condensation reactions with 4-ethyl-3-(4-morpholin-4-yl-piperidin-1-yl)-α,α-dimethylphenylcarbinol (III) under the actions of catalysts to obtain 6-cyano-2-[2-[4-ethyl-3-(4-morpholin-4-yl-piperidin-1-yl)phenyl]propane-2-yl]-1H-indole-3-carboxylic acid methyl ester or 6-cyano-2-[2-[4-ethyl-3-(4-morpholin-4-yl-piperidin-1-yl)phenyl]propane-2-yl]-1H-indole-3-carboxylic acid ethyl ester (IV) respectively; then 6-cyano-2-[2-[4-ethyl-3-(4-morpholin-4-yl-piperidin-1-yl)phenyl]propane-2-yl]-1H-indole-3-carboxylic acid methyl ester or 6-cyano-2-[2-[4-ethyl-3-(4-morpholin-4-yl-piperidin-1-yl)phenyl]propane-2-yl]-1H-indole-3-carboxylic acid ethyl ester (IV) goes through hydrolysis reaction to obtain 6-cyano-2-[2-[4-ethyl-3-(4-morpholin-4-yl-piperidin-1-yl)phenyl]propane-2-yl]-1H-indole-3-carboxylic acid (V); 6-cyano-2-[2-[4-ethyl-3-(4-morpholin-4-yl-piperidin-1-yl)phenyl]propane-2-yl]-1H-indole-3-carboxylic acid (V) goes through cyclization reaction under the action of alkali accelerant to obtain Alectinib (I).

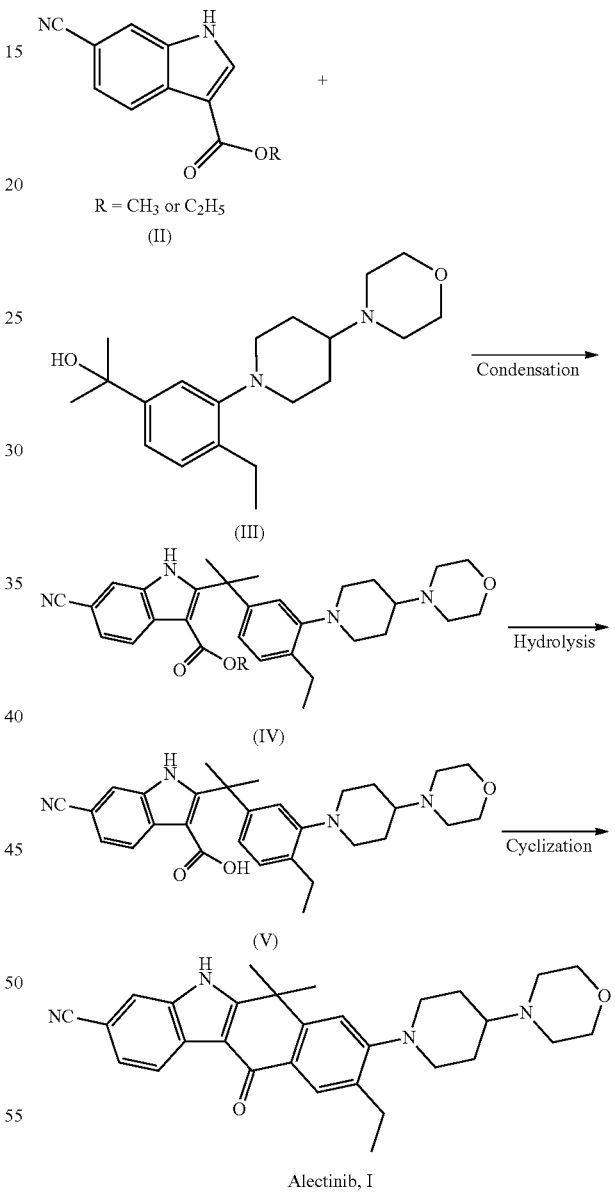

Alectinib, I

Additionally, this invention has also proposed auxiliary technical schemes as follows:

Preparation steps of the above-mentioned raw materials, 6-cyano-1H-indole-3-carboxylic acid methyl ester or 6-cyano-1H-indole-3-carboxylic acid ethyl ester (II) comprise: 6-cyano-1H-indole (VI) first goes through acylation reactions with trichloro-acetic chloride, and then goes through esterification reactions with the methanol or ethanol respectively to obtain 6-cyano-1H-indole-3-carboxylic acid methyl ester or 6-cyano-1H-indole-3-carboxylic acid methyl ester (II).

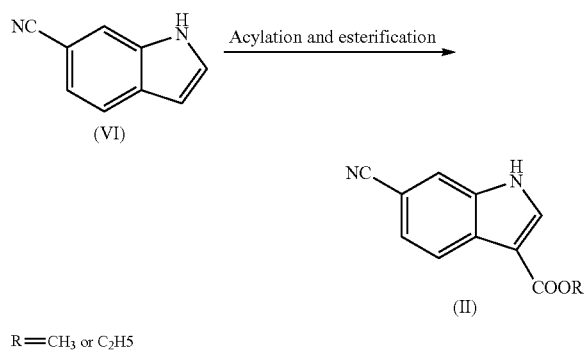

R = CH₃ or C₂H₅

Preparation steps of the aforesaid raw material, 4-ethyl-3-(4-morpholin-4-yl-piperidin-1-yl)-α,α-dimethylphenylcarbinol (III) comprise: 4-acetyl-2-bromo-ethylbenzene (VII) goes through substitution reaction with 4-(morpholin-4-yl) piperidin (VIII) to obtain 4-acetyl-2-(4-morpholin-4-yl-1-piperidinyl)ethylbenzene (IX); then, 4-acetyl-2-(4-morpholin-4-yl-1-piperidinyl)ethylbenzene (IX) goes through Grignard reaction to obtain 4-ethyl-3-(4-morpholin-4-yl-piperidin-1-yl)-α,α-dimethylphenylcarbinol (III).

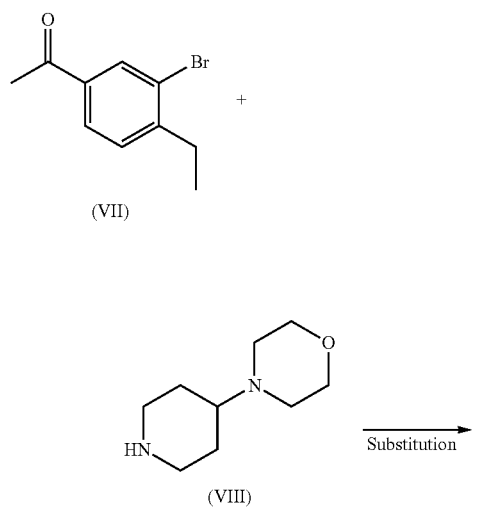

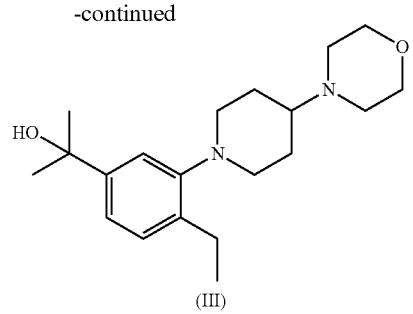

Molar ratio of the aforesaid raw materials, 6-cyano-1H-indole-3-carboxylic acid methyl ester or 6-cyano-1H-indole-3-carboxylic acid ethyl ester (II) of condensation reaction and the compound 4-ethyl-3-(4-morpholin-4-yl-piperidin-1-yl)-α,α-dimethylphenylcarbinol (III) is 1:0.5-1.5, and 1:0.9-1.1 is preferred.

Catalysts of the aforesaid condensation reactions include trifluoroacetic acid, trifluoromethanesulfonic acid, methanesulfonic acid, boron trifluoride or boron chloride, and trifluoroacetic acid or boron trifluoride is preferred.

Solvent of the aforesaid condensation reactions is dichloromethane, chloroform, 1,2-Dichloroethane, acetonitrile, methylbenzene, tetrahydrofuran, dimethyl carbonate or dioxane, and dichloromethane or tetrahydrofuran is preferred.

Temperature of the aforesaid condensation reactions is −25-50° C., and 0-25° C. is preferred.

Solvent of the aforesaid hydrolysis reaction is methyl alcohol, ethyl alcohol, isopropyl alcohol, trifluoroethanol, hexafluoroisopropanol or 1-fluoro-2-chloroethane, and trifluoroethanol is preferred.

Alkali accelerant of the aforesaid cyclization reactions is triethylamine, pyridine, N-methylmorpholine, diisopropylethylamine, 4-dimethylaminopiperidine, potassium carbonate, lithium carbonate or potassium tert-butoxide, and pyridine or diisopropylethylamine is preferred.

Temperature of aforesaid cyclization reactions is 50-120° C., and 80-100° C. is preferred.

Compared to the existing technologies, the preparation method for Alectinib (I) involved in this invention features good availability of raw materials, simple and direct processes and economy and environmental protection, which thus is beneficial to the industrialized production of the active pharmaceutical ingredients, and can promote its economic and technical development.

DETAILED DESCRIPTION OF THE PREFERRED EMBODIMENTS

A detailed and unrestricted description is further made as follows against the technical scheme of this invention in combination with several preferred embodiments.

For preparation of the starting materials, 6-cyano-1H-indole(VI) and 4-(morpholin-4-yl)piperidin (VIII), see "Organic Letters, 8(10), 1975-1978, 2006" and "Bioorganic & Medicinal Chemistry Letters, 22(9), 3157-3162, 2012" respectively for their preparation methods of the same compounds.

Embodiment I

Add 6-cyano-1H-indole-3-carboxylic acid methyl ester (II) (2.0 g, 10 mmol), 4-ethyl-3-(4-morpholin-4-yl-piperidin-1-yl)-α,α-dimethylphenylcarbinol (III) (3.3 g, 10 mmol) and 50 mL dichloromethane into the reaction flask, and lower the temperature to 0-5° C.; then, add in the trifluoroacetic acid (0.12 g, 1 mmol), and keep stirring for 30 minutes; raise the temperature to the ambient temperature and continue the reactions for 2-4 hours; detect the end of reactions with TLC. Wash the reaction system with water, 10% sodium bicarbonate solution and saturated salt solution respectively, and dry it with anhydrous sodium sulfate; then, conduct concentration operations until solid particle formation. Recrystallize the obtained crude product with n-hexane and ethyl acetate (1:1, V/V), and dry it by vacuum to obtain the off-white solid, 6-cyano-2-[2-[4-ethyl-3-(4-morpholin-4-yl-piperidin-1-yl)phenyl]propane-2-yl]-1H-indole-3-carboxylic acid methyl ester (IV), 4.1 g; yield rate is 79.8%; mass spectrum (EI): m/z 515 (M+H).

Embodiment II

Add 6-cyano-1H-indole-3-carboxylic acid methyl ester (II) (2.2 g, 10 mmol), 4-ethyl-3-(4-morpholin-4-yl-piperidin-1-yl)-α,α-dimethylphenylcarbinol (III) (3.3 g, 10 mmol) and 50 mL tetrahydrofuran into the reaction flask, and lower the temperature to 0-5° C.; then, add in the ether solution of boron trifluoride (1.4 g, 10 mmol), and conduct stirring reactions for 30 minutes; rise the temperature to the ambient temperature and continue the reactions for 2-4 hours; detect the end of reactions with TLC. Quench the reactions with water, and extract the reaction system with dichloromethane for three times; the organic phases use water, 10% sodium bicarbonate solution and saturated salt solution respectively; then dry the reaction system with anhydrous sodium sulfate and concentrate it until solid particle formation. Recrystallize the obtained crude product with n-hexane and ethyl acetate (1:1, V/V), and dry it by vacuum to obtain the off-white solid, 6-cyano-2-[2-[4-ethyl-3-(4-morpholin-4-yl-piperidin-1-yl)phenyl]propane-2-yl]-1H-indole-3-carboxylic acid methyl ester (IV), 3.82 g; yield rate is 72.3%; mass spectrum (EI): m/z 529 (M+H).

Embodiment III

Add 6-cyano-2-[2-[4-ethyl-3-(4-morpholin-4-yl-piperidin-1-yl)phenyl]propane-2-yl]-1H-indole-3-carboxylic acid methyl ester (IV) (2.57 g, 5 mmol) and 15 mL trifluoroethanol into the reaction flask in the nitrogen atmosphere; then, add in 2 mL trimethylchlorosilane under the temperature of 5-10° C. and conduct stirring operations for 3 hours. Add in 15 mL acetone, and add in 9 mL 1M sodium hydroxide solution and 3 mL 1M potassium dihydrogen phosphate solution drop by drop; slowly stir to crystallize the solid. Filter the reaction system, and wash the obtained solid with water and acetone (1:1, V/V); then dry it to obtain the off-white solid 6-cyano-2-[2-[4-ethyl-3-(4-morpholin-4-yl-piperidin-1-yl)phenyl]propane-2-yl]-1H-indole-3-carboxylic acid (V), 2.36 g; yield rate is 94.4%; mass spectrum (EI): m/z 501 (M+H).

Embodiment IV

Add 6-cyano-2-[2-[4-ethyl-3-(4-morpholin-4-yl-piperidin-1-yl)phenyl]propane-2-yl]-1H-indole-3-carboxylic acid (V) (2.5 g, 5 mmol), 6 mL N,N-diisopropylethylamine and 50 mL N,N-dimethylacetamide into the reaction flask in the nitrogen atmosphere; rise the temperature to 90-95° C. and conduct stirring reactions for 1-2 hours; adds in 20 mL methyl alcohol and 30 mL water to crystallize the solid.

Filter the reaction system, and recrystallize the crude product with water and methyl alcohol to obtain white solid Alectinib (I), 2.1 g; yield rate is 87.1%; mass spectrum (EI): m/z 483 (M+H).

Embodiment V

Add 6-cyano-1H-indole (VI) (2.84 g, 20 mmol) and 50 mL dioxane into the reaction flask, and lower the temperature to 5° C.; add in pyridine (16.1 mL, 200 mmol) and trichloro-acetic chloride (11.1 mL, 100 mmol) drop by drop while stirring. After end of titration, raise the temperature to 70-80° C., and leave 3-4 hours for reactions; detect end of the reactions with TLC. Lower the temperature to the ambient temperature, and pour the reaction liquid into the ice water; extract the reaction liquid with ethyl acetate for three times, and combine the organic phases; then wash them with water and saturated salt solution successively, and dry them with anhydrous sodium sulfate. Concentrate them to dry state and dissolve the residue into 100 ml methyl alcohol; add in 0.3 g sodium hydroxide, and heat the solution to backflow and react for 1 hour. Distil off most of the solvent under normal pressure, add in ethyl acetate and wash with water twice. Dry the solution with anhydrous sodium sulfate and concentrate it to remove the solvent. Recrystallize the residue with n-hexane and ethyl acetate to obtain the white solid, 6-cyano-1H-indole-3-carboxylic acid methyl ester (II), 3.72 g; yield rate is 93.0%; mass spectrum (EI): m/z 201 (M+H).

Embodiment VI

Add 6-cyano-1H-indole (VI) (2.84 g, 20 mmol) and 50 mL dioxane into the reaction flask, and lower the temperature to 5° C.; add in pyridine (16.1 mL, 200 mmol) and trichloro-acetic chloride (11.1 mL, 100 mmol) drop by drop while stirring. After end of titration, raise the temperature to 70-80° C., and have them react for 3-4 hours; detect end of the reactions with TLC. Lower the temperature to the ambient temperature, and pour the reaction liquid into the ice water; extract the reaction liquid with ethyl acetate for three times, and combine the organic phases; then wash them with water and saturated salt solution successively, and dry them with anhydrous sodium sulfate. Concentrate them to dry state and dissolve the residue into 100 ml ethyl alcohol; add in 0.4 g potassium hydroxide, and heat the solution to backflow and react for 1 hour. Distil off most of the solvent under normal pressure, add in ethyl acetate and wash with water twice. Dry the solution with anhydrous sodium sulfate and concentrate it to remove the solvent. Recrystallize the residue with n-hexane and ethyl acetate to obtain the white solid, 6-cyano-1H-indole-3-carboxylic acid methyl ester (II), 3.86 g; yield rate is 90.2%; mass spectrum (EI): m/z 215 (M+H).

Embodiment VII

Add 4-acetyl-2-bromo-ethylbenzene (VII) (2.26 g, 10 mmol), 4-(morpholin-4-yl) piperidin (VIII) (2.55 g, 15 mmol), potassium tert-butoxide (2.24 g, 20 mmol) and 50 mL dimethyl sulfoxide into the microwave reaction flask; place the reaction flask into the microwave reactor (700 W), and have them react for 5-10 minutes. Cool the reaction flask to ambient temperature, pour the reaction liquid into the ice water and keep stirring for 10 minutes; filter the solution and filter out the insoluble substances; extract the solution with ethyl acetate for three times, and combine the organic phases; then wash them with water saturated ammonium chloride and saturated salt solution successively, and dry them with anhydrous sodium sulfate. Concentrate them to dry state, and recrystallize the residue with n-hexane and ethyl acetate to obtain the white solid, 4-acetyl-2-(4-morpholin-4-yl-1-piperidinyl)ethylbenzene (IX), 3.0 g; yield rate is 94.9%; mass spectrum (EI): m/z m/z 317 (M+H).

Embodiment VIII

Add 4-acetyl-2-(4-morpholin-4-yl-1-piperidinyl)ethylbenzene (IX) (1.58 g, 5 mmol) and 50 mL tetrahydrofuran into the reaction flask, and lower the temperature to 0-5° C.; add in 10 mL tetrahydrofuran solution of methylmagnesium chloride (0.4 mL, 10 mmol) drop by drop while stirring. After end of titration, have them react for 2 hours under ambient temperature. Pour the reaction liquid into the ice salt water; extract the reaction liquid with ethyl acetate for three times, and combine the organic phases; then wash them with water and saturated salt solution successively, and dry them with anhydrous sodium sulfate. Concentrate them to dry state, and recrystallize the residue with n-hexane to obtain grey white solid 4-ethyl-3-(4-morpholin-4-yl-piperidin-1-yl)-α,α-dimethylphenylcarbinol (III), 1.44 g; yield rate is 86.5%; mass spectrum (EI): m/z 333 (M+H).

It needs to be noted that the above-mentioned embodiments are only used to describe the technical thought and characteristics of the invention and the purposes are to get the persons familiar with this technology understand the content of the invention and implement the invention accordingly. They shall not be used to restrict the protection scope of this invention. All equivalent changes and modifications made upon the spiritual essence of the invention shall be included in the protection scope of the invention.

The invention claimed is:

1. A method for preparing Alectinib comprising:
condensation reacting material selected from the group consisting of 6-cyano-1H-indole-3-carboxylic acid methyl ester and 6-cyano-1H-indole-3-carboxylic acid ethyl ester with 4-ethyl-3-(4-morpholin-4-yl-piperidin-1-yl)-α,α-dimethylphenylcarbinol in the presence of a catalyst to obtain one of 6-cyano-2-[2-[4-ethyl-3-(4-morpholin-4-yl-piperidin-1-yl)phenyl]propane-2-yl]-1H-indole-3-carboxylic acid methyl ester and 6-cyano-2-[2-[4-ethyl-3-(4-morpholin-4-yl-piperidin-1-yl) phenyl]propane-2-yl]-1H-indole-3-carboxylic acid ethyl ester;
hydrolyzing the one of the 6-cyano-2-[2-[4-ethyl-3-(4-morpholin-4-yl-piperidin-1-yl)phenyl]propane-2-yl]-1H-indole-3-carboxylic acid methyl ester and 6-cyano-2-[2-[4-ethyl-3-(4-morpholin-4-yl-piperidin-1-yl) phenyl]propane-2-yl]-1H-indole-3-carboxylic acid ethyl ester to obtain 6-cyano-2-[2-[4-ethyl-3-(4-morpholin-4-yl-piperidin-1-yl)phenyl]propane-2-yl]-1H-indole-3-carboxylic acid; and
cyclizing the 6-cyano-2-[2-[4-ethyl-3-(4-morpholin-4-yl-piperidin-1-yl) phenyl]propane-2-yl]-1H-indole-3-carboxylic acid with an alkali accelerant to obtain Alectinib.

2. The method according to claim 1, wherein the material selected from the group consisting of 6-cyano-1H-indole-3-carboxylic acid methyl ester and 6-cyano-1H-indole-3-carboxylic acid ethyl ester is prepared via acylating 6-cyano-1H-indole with trichloro-acetic chloride, and then esterificating with methanol or ethanol respectively.

3. The method according to claim 1, wherein the 4-ethyl-3-(4-morpholin-4-yl-piperidin-1-yl)-α,α-dimethylphenylcarbinol is prepared via substitute reacting 4-acetyl-2-bromo-ethylbenzene with 4-(morpholin-4-yl) piperidin to obtain 4-acetyl-2-(4-morpholin-4-yl-1-piperidinyl)ethylbenzene, and Grignard reacting the 4-acetyl-2-(4-morpholin-4-yl-1-piperidinyl)ethylbenzene.

4. The method according to claim 1, wherein a molar ratio of the material selected from the group consisting of 6-cyano-1H-indole-3-carboxylic acid methyl ester and 6-cyano-1H-indole-3-carboxylic acid ethyl ester and the 4-ethyl-3-(4-morpholin-4-yl-piperidin-1-yl)-α,α-dimethylphenylcarbinol is 1:0.5-1.5.

5. The method according to claim 1, wherein the catalyst is selected from the group consisting of trifluoroacetic acid, trifluoromethanesulfonic acid, methanesulfonic acid, boron trifluoride and boron chloride.

6. The method according to claim 1, wherein the step of condensation reacting is performed using a solvent selected from the group consisting of dichloromethane, chloroform, 1,2-Dichloroethane, acetonitrile, methylbenzene, tetrahydrofuran, dimethyl carbonate and dioxane.

7. The method according to claim 1, wherein the step of condensation reacting is performed at a temperature of −25-50° C.

8. The method according to claim 1, wherein the step of hydrolyzing is performed using a solvent selected from the group consisting of methyl alcohol, ethyl alcohol, isopropyl alcohol, trifluoroethanol, hexafluoroisopropanol and 1-fluoro-2-chloroethane.

9. The method according to claim 1, wherein alkali accelerant is selected from the group consisting of triethylamine, pyridine, N-methylmorpholine, diisopropylethylamine, 4-dimethylaminopiperidine, potassium carbonate, lithium carbonate and potassium tert-butoxide.

10. The method according to claim 1, wherein the step of cyclizing is performed at a temperature of 50-120° C.

* * * * *